US00PP13158P2

(12) United States Plant Patent
Hanes

(10) Patent No.: US PP13,158 P2
(45) Date of Patent: Oct. 29, 2002

(54) GERANIUM PLANT NAMED 'FREE SALMON'

(75) Inventor: Mitchell Eugene Hanes, Morgan Hill, CA (US)

(73) Assignee: Goldsmith Plants, Inc., Gilroy, CA (US)

( * ) Notice: Subject to any disclaimer, the term of this patent is extended or adjusted under 35 U.S.C. 154(b) by 26 days.

(21) Appl. No.: 09/915,577

(22) Filed: Jul. 27, 2001

(51) Int. Cl.[7] ..... A01H 5/00
(52) U.S. Cl. ..... Plt./332
(58) Field of Search ..... Plt./332

*Primary Examiner*—Kent L. Bell
(74) *Attorney, Agent, or Firm*—Rothwell, Figg, Ernst & Manbeck

(57) ABSTRACT

A geranium cultivar particularly distinguished by green foliage, salmon flower color, and semi-double flowers on large umbels, fast rooting and exhibits vigorous growth.

2 Drawing Sheets

GENUS AND SPECIES

*Pelargonium peltatum.*

VARIETY DENOMINATION

'Free Salmon'.

BACKGROUND OF THE NEW PLANT

The present invention comprises a new and distinct cultivar of geranium, botanically known as *Pelargonium peltatum*, and hereinafter referred to by the cultivar name 'Free Salmon'. The new cultivar is propagated from a seedling resulting from the cross of an unnamed and unpatented, red, semi-double flowered plant of proprietary breeding line 7391-3 as the female parent and an unnamed and unpatented, pink, semi-double flowered plant of proprietary breeding line 7395-1 as the male parent.

'Free Salmon' is a product of a planned breeding program intended to create new geranium cultivars with salmon colored flowers, semi-double flower form, dark green foliage, vigorous growth and superior cutting productivity.

The new cultivar was created in 1998 in Gilroy, Calif. and has been asexually reproduced repeatedly by cuttings in Gilroy, Calif. over a two year period. The plant has also been trialed at Gilroy, Calif. and Andijk, The Netherlands. The plant has been found to retain its distinctive characteristics through successive propagations; and this novelty is firmly fixed.

DESCRIPTION OF PHOTOGRAPH

This new geranium plant is illustrated by the accompanying photograph which shows blooms, buds, and foliage of the plant in full color, the colors shown being as true as can be reasonably obtained by conventional photographic procedures.

DESCRIPTION OF THE NEW CULTIVAR

Figure 1:
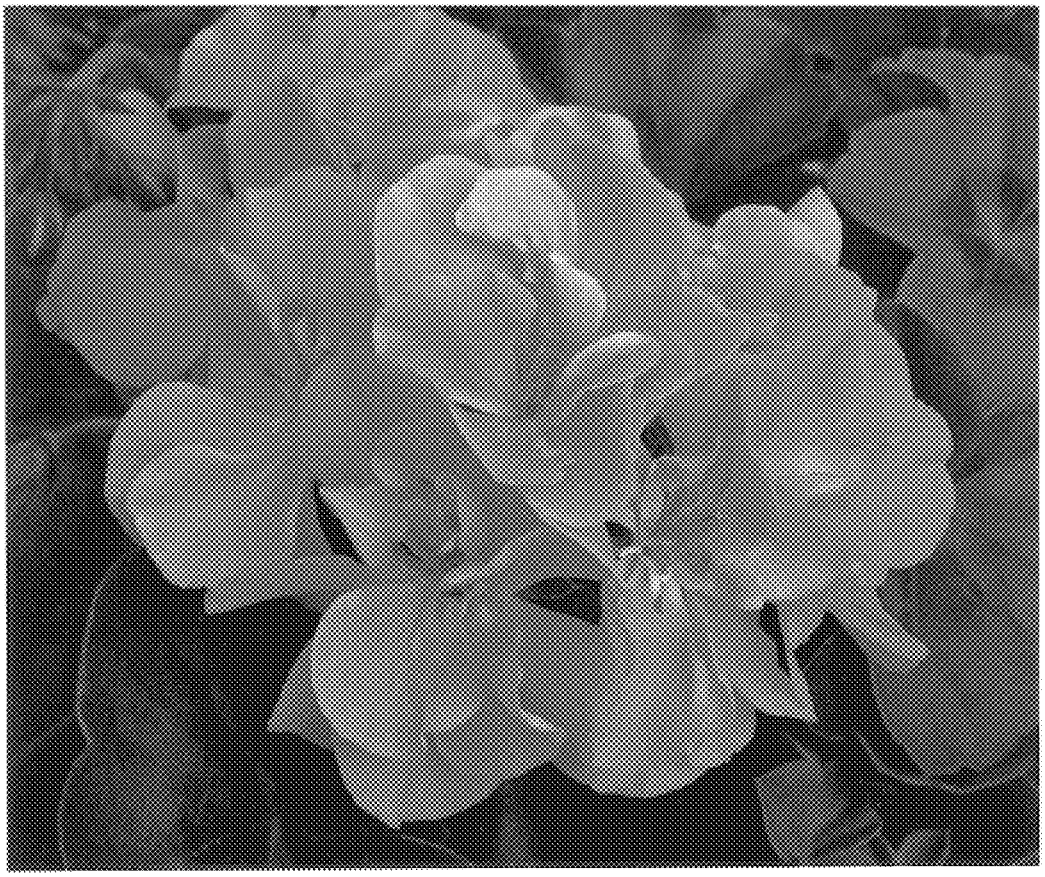
FIG. 1 shows the blooms of the plant.
Figure 2:
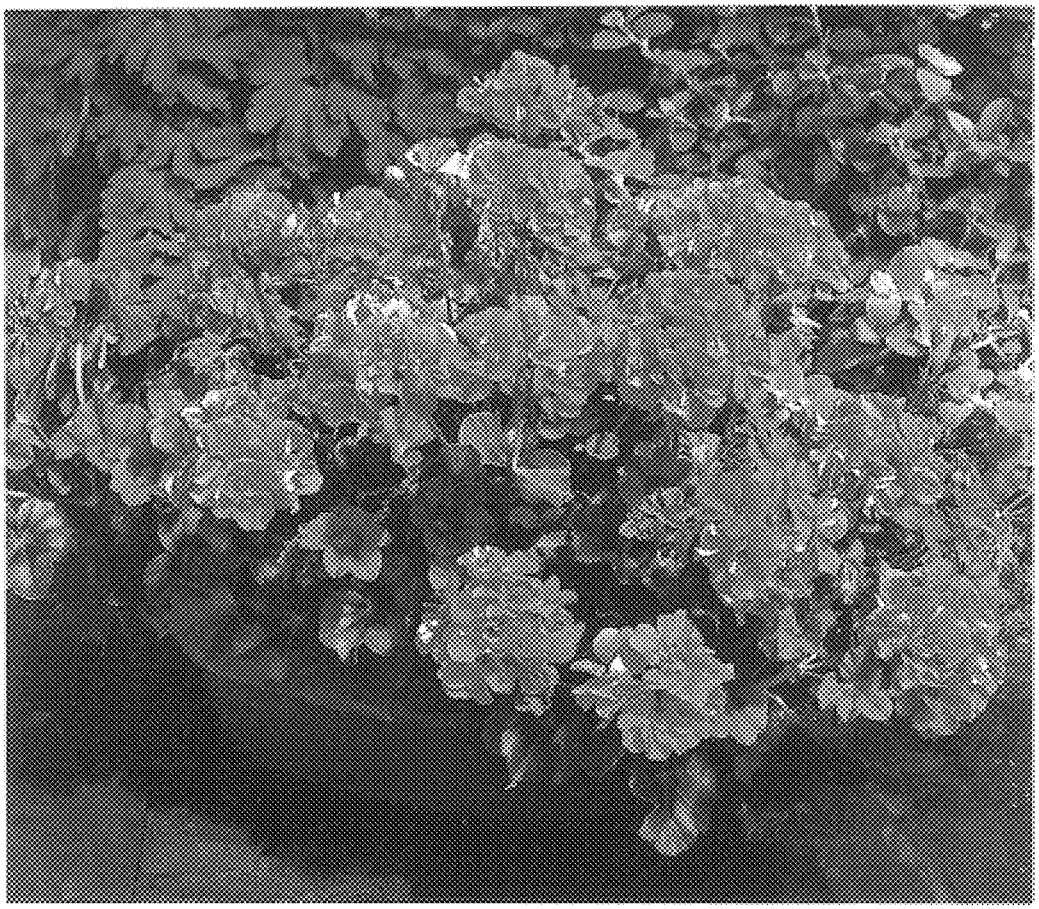
FIG. 2 shows the overall plant habit.

The following detailed descriptions set forth the distinctive characteristics of 'Free Salmon'. The data which defines these characteristics were collected from asexual reproductions carried out in Gilroy, Calif. The plant history was taken on seven month old plants grown in 8 inch pots, blossomed under natural light in a greenhouse and color readings were taken in the greenhouse in Gilroy, Calif. Color references are primarily to The R.H.S. Colour Chart of The Royal Horticultural Society of London (R.H.S.).

DETAILED BOTANICAL DESCRIPTION

Form: Upright, spreading.
Height: From soil level to top of plant (excluding blooms)—15–18 cm; from soil level to top of umbels—20–25 cm.
Width: 45–55 cm; if lateral branches are outstretched the width is 70–75 cm.
Time to produce a finished flowering plant: 13 weeks.
Outdoor plant performance: Good weather tolerance.
Time to initiate roots: 8–10 days.
Time to develop roots: 26–28 days.
Root description: White, slightly pubescent, fibrous yet coarse.

THE LEAVES

Length: 3.7–5.0 cm.
Width: 5.5–8.5 cm depending on age.
Apex description: Cuspidate/mucronate.
Base description: Cordate, two bottom lobes are slightly imbricate.
Shape: Reniform, seven lobes with cuspidate/mucronate apice.
Margin: Entire, ciliate.
Texture: Lightly pubescent, somewhat succulent.
Ribs and veins: Palmate, 2.0–4.0 cm long.
Color:
*Upper side.*—A shade darker than yellow-green RHS 146A but lighter than yellow-green RHS 147A.
*Upper side.*—Yellow-green RHS 146A; Ribs and veins—Yellow-green RHS 146A.
Zonation: 2–3 cm wide with a shade of RHS 200B or 200C down the middle of the leaf. The zone color varies depending on the amount of sunlight the leaf receives. In lower light levels and with excessive lush growth, the zone is not visible.
Petiole length: 4.0–8.5 cm depending on age of the leaf.
Petiole diameter: 2.0 mm.

Petiole color: Yellow-green RHS 144B.
Lateral branch length: 11–43 cm.
Internode length: 2.5–5.5 cm.
Lateral branch color: Yellow-green RHS 144B.

THE BUD

Diameter: 7.0–8.0 mm.
Length: 1.2–1.5 cm.
Shape: Elliptic.
Color when sepals first divide: Red RHS 43C.
Number of sepals: Five, pubescent with long white hairs, sepals are recurved/reflexed in open flower.
Length of sepals: 1.5 cm.
Width of sepals: 3.0–4.0 mm.
Apex description: Acuminate.
Base description: Truncate.
Sepal color in an open flower: Upper and lower surfaces are yellow-green RHS 144A.

THE FLOWER

Flowering season: Continuous throughout the year.
Size: Approximately 4.5–5.0 cm in diameter, 2.0–2.5 cm in depth.
Form: Polypetalous.
Petals/petaloids: 9–11 mostly imbricate petals, 2.5–3.0 cm in length, 1.9–2.2 cm in width, 2–4 petaloids; Shape: spatulate.
Apex shape: Obtuse/retuse.
Base shape: Attenuate.
Margin: Serrulate.
Upper petal/petaloid color:
*Upper petal surface.*—Salmon RHS 52A; upper two petals have a small macule of red RHS 46A.
*Petal under surface.*—Salmon RHS 49D with numerous streaks of pink RHS 52C and a margin of RHS 52C.
*Upper petaloid color.*—Salmon RHS 52A.
Lower petal/petaloid color: Lower petal: Salmon RHS 52A on both surfaces; Lower petaloid color is salmon RHS 52A.
Color change with age: Colors do not change with age but may change with temperature and time of year.
Pedicel length: Approximately 2.5 cm.
Pedicel color: Yellow-green RHS 144A.
Flower persistence: An open flower will hold it's petals until the flower begins to dehisce, or approximately 7–10 days.

THE INFLORESCENCE

Type: An umbel composed of approximately 5–6 flowers.
Diameter: 7.0–8.0 cm.
Depth: 4.5–5.0 cm.
Peduncle length: 10.5–14.0 cm.
Peduncle color: Yellow-green RHS 144A.

THE REPRODUCTIVE ORGANS

Anthers: 7–9.
Anther color: Salmon RHS 52A prior to anthesis.
Filament color: White RHS 155A.
Pollen amount and color: Moderate, orange RHS 28A.
Pistil: 1 with a length of 8 mm.
Stigma: 6 linear lobes with a color of salmon RHS 52A.
Style: 2.0 mm with a color of yellow-green RHS 149D.
Ovary: Densely pubescent with white hairs, oblong, green drying to a light brown at maturity.
Seed number: Maximum of 5 per spike.
Seed length: 5 mm.
Seed width: 1.5 mm.
Seed color: Grey-orange RHS 177B that may darken with age.

DISEASE AND INSECT RESISTANCE

No susceptibility to disease or insects noted to date.

COMPARISON WITH KNOWN CULTIVARS

When the instant plant is compared to the female parental cultivar, an unnamed plant from proprietary breeding line 7391-3, 'Free Salmon' has a salmon colored flower versus red for the female parent. When compared to the male parental cultivar, an unnamed plant from proprietary breeding line 7395-1, 'Free Salmon' has a salmon colored flower compared to pink for the male parent.

I claim:

1. A new and distinct cultivar of geranium plant as shown and described herein.

* * * * *